US012458569B2

(12) United States Patent
Grundler et al.

(10) Patent No.: US 12,458,569 B2
(45) Date of Patent: Nov. 4, 2025

(54) RETRACTION PASTE AND CONTAINER COMPRISING THE RETRACTION PASTE

(71) Applicant: KULZER GMBH, Hanau (DE)

(72) Inventors: Andreas Grundler, Münzenberg (DE); Martin Grunwald, Pulheim (DE); Peter Deutzmann, Rommerskirche (DE)

(73) Assignee: KULZER GMBH, Hanau (DE)

( * ) Notice: Subject to any disclaimer, the term of this patent is extended or adjusted under 35 U.S.C. 154(b) by 261 days.

(21) Appl. No.: 18/267,953

(22) PCT Filed: Dec. 16, 2021

(86) PCT No.: PCT/EP2021/086175

§ 371 (c)(1),
(2) Date: Jun. 16, 2023

(87) PCT Pub. No.: WO2022/129323

PCT Pub. Date: Jun. 23, 2022

(65) Prior Publication Data

US 2024/0050321 A1 Feb. 15, 2024

(30) Foreign Application Priority Data

Dec. 18, 2020 (DE) ........................ 10 2020 134 315

(51) Int. Cl.
*A61K 6/18* (2020.01)

(52) U.S. Cl.
CPC ..................................... *A61K 6/18* (2020.01)

(58) Field of Classification Search
CPC ........................................................ A61K 6/18
See application file for complete search history.

(56) References Cited

U.S. PATENT DOCUMENTS

2012/0077142 A1 3/2012 Maurer et al.

FOREIGN PATENT DOCUMENTS

DE 102018104375 A1 8/2019
WO 2010/138433 A1 12/2010

OTHER PUBLICATIONS

International Search Report dated Mar. 21, 2022, in connection with PCT International Application No. PCT/EP2021/086175.
English translation of International Search Report dated Mar. 21, 2022, in connection with PCT International Application No. PCT/EP2021/086175.
Written Opinion in connection with PCT International Application No. PCT/EP2021/086175.
Second Page of German Office Action in connection with German Application No. 10 2020 134 315.9.

*Primary Examiner* — Benjamin J Packard
(74) *Attorney, Agent, or Firm* — Norris McLaughlin, PA

(57) ABSTRACT

The invention relates to a retraction paste comprising a composition of i) 10 to 25% by weight at least one astringent compound, ii) 50 to 75% by weight fillers, iii) 10 to 35% by weight protic liquid, and iv) 0 to 10% by weight pigments, dye and/or rheology additive, ii) the fillers comprising kaolinite and mica in the ratio of 4:1 to 1.5:1 and, the total composition of components i) to iv) in the retraction paste amounting to 100% by weight, a method for producing the retraction paste, a kit comprising a container with the retraction paste for single or repeated use, as well as a retraction paste as an agent for haemostasis.

14 Claims, 5 Drawing Sheets

RETRACTION PASTE AND CONTAINER COMPRISING THE RETRACTION PASTE

This application is a 371 of International Patent Application No. PCT/EP2021/086175, filed Dec. 16, 2021, which claims priority of German Patent Application No. 10 2020 134 315.9, filed Dec. 18, 2021, the disclosures of which patent applications are hereby incorporated herein by reference.

The invention relates to a retraction paste comprising a composition of i) 10 to 25% by weight at least one astringent compound, ii) 50 to 75% by weight fillers, iii) 10 to 35% by weight protic liquid, and iv) 0 to 10% by weight pigments, dye and/or rheology additive, ii) the fillers comprising kaolinite and mica in the ratio of 4:1 to 1.5:1 and, the total composition of components i) to iv) in the retraction paste amounting to 100% by weight, a method for producing the retraction paste, as well as a kit comprising a container with the retraction paste for single or repeated use. The retraction paste is a dental retraction composition that may be present as paste or gel and comprises a protic liquid as well as specific solids, at least one solid thereof being able to absorb additional liquid. The solids form a mixture comprising at least one silicate from the clay mineral group and one silicate from the mica mineral group which are preferably used in a defined weight ratio to each other.

The accuracy of an impression of preparation margins has a direct influence on the marginal quality of fixed dentures (restorations) and thus directly affects the long-term success of the restoration. Even if impression materials nowadays have a high degree of hydrophilicity and flowability, correct draining and exposure of the preparation margin is essential, especially in case of subgingivally located preparation margins. Therefore, the sulcus must first be temporarily opened and freed from fluids such as blood or sulcus fluid. Known are the mechanical thread technique and the use of retraction pastes having a chemical effect. Astringents and vasoconstrictors are used as chemical components for haemostasis.

Various techniques, such as the thread technique and the use of retraction pastes, are known for widening the gingiva to expose the preparation margin of a ground tooth stump that is to be provided with a fixed restoration or such as according to the double-crown technique for removable restorations.

Cotton threads treated with astringents are usually used as retraction threads to absorb the fluid in the sulcus. For this technique, due to the retraction threads to be inserted, which are impregnated with a dried astringent, a sufficient amount of sulcus fluid is then necessary in order to subsequently be able to remove the retraction threads without damaging the sulcus.

Application of the thread technique is time-consuming and requires careful removal of the inserted thread so as not to reopen the previously stopped bleeding in the sulcus wound by carelessly removing the thread. In addition, the threads are often inserted into the sulcus to be exposed/expanded using dental instruments and then pushed further into the sulcus with the instrument. In doing so, the root skin (Sharpey's fibres or desmodontal fibres, respectively) can be injured due to slipping, piercing, lack of accessibility or even carelessness. The Sharpey's fibres belong to the root skin and are fused with both the root element of the tooth root and the alveoli in the jawbone. The function of the Sharpey's fibres is to cushion the tensile forces of the teeth to the jawbone. Without Sharpey's fibres, the jawbone reacts with degradation. Therefore, injury to the Sharpey's fibres must absolutely be avoided during the treatment of a patient for the fabrication of fixed dentures, i.e. a fixed restoration.

In the state of the art, there are retraction pastes known for which it is sometimes time-consuming and difficult to completely remove an uncured paste from the sulcus before taking the impression. Usually, the retraction paste is removed with a water stream. However, it may happen that the paste is too deep in the sulcus and is then difficult to remove. Remains of the retraction paste prevent the impression material from flowing into the sulcus on the one hand and can lead to irritation of the sulcus and inflammation of the Sharpey's fibres on the other hand. Likewise, remains of the retraction paste can impair the hardening reaction of an impression material that has flowed into the sulcus. Hardening retraction pastes may be removable with less effort in some cases, but the difficulty here is the insertion into the narrow sulcus due to mostly low viscosity. Once the retraction pastes or threads are placed in the sulcus, the respective application time varies from 1 minute to 15 minutes. If the application time is too long, there is a risk of tissue damage. Sometimes parts of the retraction thread remain in the sulcus and cause irritation or inflammation.

In addition, sufficient expansion of the sulcus by means of a retraction paste must be ensured in order to avoid tearing off impression material when removing the cured impression material in the sulcus, which can lead to inflammation and reversible or irreversible tissue damage there. Irritation or damage to the Sharpey's fibres must absolutely be avoided.

Therefore, it was an object of the invention to provide a retraction paste that does not require the use of textile or woven retraction threads for sulcus dilation and haemostasis, but can still be used together with retraction threads or retraction threads not impregnated with astringents, i.e. untreated threads, if required. A further object of the invention was to provide a retraction paste which, on the one hand, meets the requirements for the astringent effect and therefore has a haemostatic effect in the vicinity of the sulcus. Furthermore, the retraction paste should prevent the retraction of the opened sulcus immediately after the opening of the sulcus and should preferably be able to be introduced into the sulcus under increased pressure and there preferably counteract the retraction of the sulcus in a self-stabilised manner. Moreover, the retraction paste should preferably be able to absorb fluid and thus dry out the sulcus. In addition, it was the object to adjust the hydrophilicity and lipophilicity of the retraction paste in such a way that, on the one hand, it flows easily into the dilated sulcus during its application and, on the other hand, it can be introduced into the sulcus to be dilated through a blunt, preferably thin cannula without applying too much pressure. Once discharged, absorption of fluid in the sulcus shall then be carried out and additionally the astringent effect should begin. With a very well-balanced interaction of the aforementioned requirements, injury to the Sharpey's fibres can be avoided and yet good dilatation of the sulcus can be achieved. It is subsequently a further object for the retraction paste with fluid from the sulcus to be easily and completely removable from the sulcus with water, preferably without using mechanical measures, and for this removal to be easily followed visually. In addition, it was the object to provide a composition that can be introducible into the sulcus in existing applicators through very thin and possibly curved cannulas. Furthermore, the retraction paste should be lipophilic on the one hand and at the same time preferably offer sufficient resistance to the gingiva so that the gingiva does not press the paste out of the sulcus after application and no sulcus widening takes place de facto. This behaviour can be verified, for example, by measuring the storage modulus of the paste by means of a rheometer, or—even more practically—by determining the displacement resistance when displacing the paste by means of a tactility meter/texture analyser.

A subject matter of the invention is a retraction paste according to claim 1, a method according to claim 9 as well as a kit according to claim 10, preferred embodiments are in the subclaims, wherein the invention is disclosed in detail in the description.

According to the invention, a retraction paste is provided that comprises an astringent agent, preferably aluminium chloride, for haemostasis. The consistency of the retraction paste according to the invention is such that it allows displacement to widen the sulcus of the gingiva.

A subject matter of the invention is a retraction paste comprising i) 1 to 25% by weight of at least one astringent compound,
ii) 50 to 75% by weight fillers,
iii) 10 to 35% by weight protic liquid, and
iv) 0 to 15% by weight pigments, dye and/or rheology additive,
ii) the fillers comprising kaolinite and mica in the ratio of 4:1 to 1.5:1 and, the total composition of components i) to iv) in the retraction paste amounting to 100% by weight.

The astringent compound may be selected from organic astringent compounds or from inorganic astringent compounds. The organic astringent compounds may preferably be present in an amount of 1 to 25% by weight, preferably of 3 to 20% by weight. Inorganic astringent compounds are usually present from 5 to 25% by weight, preferably from 10 to 25 by weight.

A particularly preferable retraction paste comprises i) 10 to 25% by weight of at least one astringent compound, in particular 10 to 20% by weight,
ii) 50 to 75% by weight fillers,
iii) 10 to 35% by weight protic liquid, in particular 15 to 28% by weight, preferably 16 to 28 by weight, and
iv) 0 to 10% by weight pigments, dye and/or rheology additive,
ii) the fillers comprising kaolinite and mica in the ratio of 4:1 to 1.5:1, in particular 3.5:1 to 2:1, preferably 3:1 to 1.5:1, and, the total composition of components i) to iv) in the retraction paste amounting to 100% by weight.

The consistency of the retraction paste according to the invention is adjusted such that it is able to form stable thread-like structure or thread-like structures when being conveyed from syringes, ampoules and cartridges, in particular PLT cartridges (PLT: Preloaded Tip=having an integrated canula or from a syringe having a put-on canula. For application from a syringe e.g. having a Luer lock connection, canulas with a gauge size of 24 to 17 or an outer diameter of 0.55 to 1.4 mm (EN ISO 9626), respectively, are suitable. Preferably, canulas having a thin-walled canula with an internal pipe diameter of greater 0.343 to 1.156 depending on the gauge size used.

Particularly preferred are extra thin-walled canulas with an internal pipe section of 0.460 to 1.244 mm internal pipe section depending on the gauge size. Using particularly thin-walled canulas considerably reduces the squeezing force for the user. The canulas are preferably bent between 20° and 60° and have a length of 9 mm to 25 mm, preferably of 10 to 17 mm, particularly preferably of 13 mm+/−1 mm. Preferably, the inner diameter of the canula at the discharge side and at the side of the container is basically the same, preferably identical.

When using small cartridges, also referred to as PLT (preloaded tips; see also drawing No. 7 and 11), they preferably have an integrated canula-like outlet area, that may have a length between 8 mm and 20 mm, with an outer diameter of 0.8 mm to 1.6 mm, preferably between 1.0 mm and 1.3 mm and an inner diameter of 0.4 mm to 1.3 mm, preferably between 0.6 mm and 0.9 mm.

The particular advantage of the thread-like structure of the retraction paste is that it can be brought into the sulcus and dilates the sulcus or keeps the dilated sulcus open, as well as causes a haemostasis at the same time. The properties of the thread-like structure applied by means of the retraction paste enable a very gentle application of the retraction paste without affecting or injuring the Sharpey's fibers. It is assumed that the stability of the retraction paste in the sulcus is enabled by interlocking of elastic and tough mica lamellae to the lateral restoring force of the sulcus.

According to a particularly preferred alternative, a subject matter of the invention is a retraction paste comprising i) 1 to 25% by weight, in particular 10 to 25% by weight, of at least one astringent compound,
ii) 50 to 75% by weight fillers, in particular 55 to 70% by weight, the fillers kaolinite to mica being present in the range of kaolinite to mica with 60% by weight and 40% by weight to 80% by weight and 20% by weight in the filler component of 100% by weight, preferably with kaolinite to mica with 60% by weight and 40% by weight to 75% by weight and 25% by weight in the filler component of 100% by weight, preferably kaolinite and mica are present in the filler component with 68% by weight and 32% by weight;
iii) 10 to 35% by weight protic liquid, in particular 16 to 28% by weight, and
iv) 0 to 10% by weight pigments, dye and/or rheology additive and, the total composition of components i) to iv) in the retraction paste amounting to 100% by weight.

According to a further preferred alternative, a subject matter of the invention is a retraction paste comprising i) 10 to 25% by weight of at least one astringent compound,
ii) 51 to 70% by weight fillers, in particular 54 to 65% by weight, in particular the fillers kaolinite to mica being present in the range of kaolinite to mica with 60% by weight and 40% by weight to 80% by weight and 20% by weight in the filler component of 100% by weight, preferably with kaolinite to mica with 60% by weight and 40% by weight to 75% by weight and 25% by weight in the filler component of 100% by weight, preferably kaolinite and mica are present in the filler component with 68% by weight and 32% by weight;
iii) 15 to 29% by weight protic liquid, in particular 18 to 28% by weight, and
iv) 0 to 10% by weight pigments, dye and/or rheology additive, the total composition of components i) to iv) in the retraction paste amounting to 100% by weight.

Preferably, the stability of the retraction paste is maintained due to interlocking of the elastic and tough mica lamellae, so that a certain application time can be ensured during the sulcus being widened constantly. The combination of the interlocking of the mica and the behaviour of the kaolinite that becomes plastically mouldable in the presence of water or also saliva enables the adjustment according to the invention of the required structural viscosity of the retraction paste. The good fissility in thin mineral lamellae along the silicate layers of the mica when used in the retraction paste enables good interlocking of these randomly arranged silicate layers and thus stabilisation of the structure of the retraction paste under great application of pressure. Because micas are fissile in thin tough and elastic lamellae along their planes. Therefore, on the one hand, the composition according to the invention allows the retraction paste to flow in well and for facilitated applicability of the retraction paste, while the structure of the retraction paste has a self-stabilising effect due to the thin mineral mica layers at the same time in case of restoring forces due to the widened sulcus.

An astringent compound is understood to mean compounds having a haemostatic effect. Astringent compounds are understood to be astringents and/or vasoconstrictors, such as adrenaline. Astringent compounds may be any compound that effects haemostasis. Usually, bleeding in the body is stopped by the formation of a blood clot (formation of a thrombus) from a special plasma protein, called fibrin. The steps in the body leading up to the formation of a thrombus are referred to as haemostasis. Haemostasis is vital to stop the bleeding occurring when blood vessels are injured.

Likewise preferred is a retraction paste, comprising i) 5 to 25% by weight, in particular 10 to 25% by weight, of at least one astringent compound, ii) 50 to 70% by weight fillers, in particular 51 to 70% by weight, preferably 54 to 65% by weight, iii) 15 to 30% by weight protic liquid, in particular 15 to 29% by weight, preferably 18 to 28 by weight, and iv) 0 to 10% by weight pigments, dye and/or rheology additive, ii) the fillers comprising kaolinite and mica in the ratio of 4:1 to 1.5:1 and, the total composition of components i) to iv) in the retraction paste amounting to 100% by weight.

Further preferred may be a retraction paste, comprising i) 10 to 20% by weight of at least one astringent compound, ii) 50 to 70% by weight fillers, iii) 15 to 30% by weight protic liquid, and iv) 0 to 10% by weight pigments, dye and/or rheology additive, ii) the fillers comprising kaolinite and mica in the ratio of 4:1 to 1.5:1 and, the total composition of components i) to iv) in the retraction paste amounting to 100% by weight.

It has been shown that, on the one hand, the smoothest pastes, concurrently having comfortable applicability through a canula for the user with very good stability of the discharged thread-like structure at the same time, are obtained using the aforementioned fillers kaolinite and mica in the ration of 4:1 bis 1,5:1 and a concurrent ratio of water to fillers of less than or equal to 1:3.5. Particularly preferred is a ratio of water to filler in the range of 1:75 to 1:3.5. The best results in relation to the aforementioned requirements can be obtained using filler contents of i) 50 to 70% by weight, in particular ii) 51 to 70% by weight, preferably iii) 54 to 65% by weight and a water content of i) 15 to 30% by weight, in particular ii) 15 to 29% by weight, preferably iii) 18 to 28% by weight. In this context, the ranges i) and i) oder ii) and ii) or iii) and iii) are preferably combined. A further criterion besides the stability for forming a preferred paste was, in addition, the formation of an as homogenous as possible, as crack-free as possible, stable thread-like structure. The formation of a homogenous closed surface of the retraction paste comfortably applicable through a canula is essential for a later precise impression of the opened sulcus to have an as plane as possible surface structure in the sulcus for impression after removal of the retraction paste using a water stream.

Kaolinite is an aluminium silicate hydrate. The fillers used in the retraction paste preferably have no surface treatment and thus are preferably not silanized.

Moreover, kaolinite is preferably present in a particle size of 0.01 to 350 μm. Preferred is ii) kaolinite of an average particle size $D_{50}$ of 0.01 to 100 micrometers, in particular $D_{50}$ of 0.01 to 10 micrometers. It may be further preferred for the kaolinite to present with a particle size of $D_{99}$ less than 60 micrometers, preferably of $D_{99}$ less than 45 micrometers, and optionally with $D_{70}$ less than 45 micrometers. Further preferably, kaolinite is present with a particle size of $D_{50}$ less than 45 micrometers and $D_{35}$ less than or equal to 2 micrometers, the remaining amount as $D_{100}$ having less than or equal to 250 micrometers. Particularly preferably, kaolinite is present with a particle size $D_{99}$ of less than or equal to 60 micrometers, further preferably less than or equal to 50 micrometers, particularly preferably less than or equal to 45 micrometers, in particular with wet sieve remains less than or equal to 2% by weight at sieving >45 μm, preferably less than or equal to 1% by weight at sieving >45 μm according to the method Zellcheming V/27.6/90. The composition of kaolinite may comprise $SiO_2$ 45 to 50% by weight, in particular 47.0 to 49.0% by weight, $Al_2O_3$ 35 to 39% by weight, in particular 36.0 to 38.0 by weight, $Fe_2O_3$ maximally 0.6% by weight, $TiO_2$ maximally 0.5% by weight; CaO maximally 0.16% by weight; MgO maximally 0.3% by weight $Na_2O$ maximally 0.1% by weight; $K_2O$ maximally 1.4% by weight, and with an ignition loss of 12.2% by weight to 13.5% by weight, in particular about approx. 12.8% by weight, determined according to DIN 51001. Preferred is kaolinite of the very general formula $Al_2[Si_2O_3(OH)_4]$, wherein further metals may be contained in the kaolinite. The particle size of the kaolinite may be determined by means of the method Zellcheming V/27.2./90 (Testing fillers and pigments—For paper, board and cardboard—Determining the grain size by sedimentation). Determination is preferably carried out by means of Sedigraph in aqueous phase. The particle size and in particular the aspect ratio of kaolin may be determined by means of the Sedigraph method using a dispersing agent. For this purpose, kaolin is dispersed and the particle size and preferably the aspect ratio is determined according to Zellcheming provision V/27.3190 (Testing fillers and pigments Determining the grain size—Sedigraph method). The method for determination by means of Sedigraph can, in particular for determining the grain size distribution in the range of fractions between <2 μm to 63 μm by means of sedimentation, preferably be combined with the determination of X-rays absorbed by the particles. The aspect ratio can be determined using two different physical determination methods. Alternatively, determination of the aspect ration can be carried out by means of sedimentation and laser diffraction.

A further possible method comprises the combination of e.g. sedimentation and laser diffraction: particle size determination by static laser diffraction analysis according to SO 13320 or particle size determination by Sedigraph method according to Zellcheming V/27.3190 or optionally be sedimentation according to V/27.2190. Kaolin is present in the form of lamellae. Advantageously, the aspect ratio of the particles, in particular of the lamellae, of the kaolin is in the range of 1:2 to 1:600, in particular of 1:2 to 1:100, preferably 1:2 to 1:40, in particular of 1:3 to 1:20. The aspect ratio is understood to be the ratio of height to lateral expansion of the particles, in particular of the lamellae. Alternatively, particularly preferred is an aspect ratio of 1:10 to 1:600.

Advantageously, the wet sieve remains, in particular for determining the particle size of the kaolinite, in particular according to the method Zellcheming V/27.6190, amounts to less than or equal to 1% by weight, preferably less than or equal to 0.01% by weight, preferably less than or equal to 0.0004% by weight for particle sizes of greater than 250 micrometers, and optionally less than 1% by weight for particle sizes greater than 45 micrometers. Moreover, it is preferred for at least 35% by weight of the particles to be less than 2 micrometers.

Moreover, it is preferred in the retraction paste for ii) mica to have an average particle size of 0.01 to 100 micrometers, in particular a particle size of $D_{99}$ less than 60 micrometers, preferably of $D_{98}$ less than 10 micrometers, and optionally with $D_{70}$ less than 4 micrometers. The method Sedigraph 5100 (method ASTM B761-06, Stokes law, directly determining the mass concentration) is used for determining the particle sizes. Mica is present in the form of lamellae. Advantageously, the aspect ratio of the particles, in particular lamellae, of the mica is in the range of 1:2 to 1:600, in particular of 1:2 to 1:100, preferably 1:2 to 1:40, in particular of 1:3 to 1:20. Alternatively particularly preferred is an aspect ratio of 1:10 to 1:600. The aspect ratio is understood to be the ratio of height to lateral expansion of the particles, in particular of the lamellae.

In general, it is accepted to combine two physical methods for determining the aspect ratios. Thus, concrete determination method are disclosed in C. Weber et al-, Clay Minerals, (2014) 49, 17-26, such as the conductometric titration, X-Ray diffraction (e.g. Huber MC 423, co anode, 40 kV, 40 mA, 2 to 115° 2Theta, step width 0.018° 2Theta, internal standard: corundum), acoustic spectroscopy (e.g. Dispersion Technology DT-1200, ultrasonic frequency 3-100 MHz), dynamic laser diffraction (e.g. Mastisizer S Long Bed, optical lens 300RF), that are completely made the content of disclosure here. For determining the pure grain size, the method Zellcheming V/27.2190 as also disclosed in Daniel Gantenbein et al, Applied Clay Science, 2011, doi: 10.1016/j.clay.2011. 04020, for determining the aspect ratio can be combined with a method considering the projection surface, such as laser diffraction.

Further inorganic fillers, organic fillers usual in the dental field may generally be added as further fillers in addition to kaolinite and mica, which may be present in the range of 0 to 10 by weight of the total content of the retraction paste, the content being included in the filler content. Metal oxides, such as preferably silicon dioxide, pyrogenic silica, precipitated silica, in particular highly-dispersed silicon dioxide, or also titanium dioxide, zinc oxide, bentonite, magnesium sulphate, may be added as further inorganic fillers. Moreover, metal oxides preferably having an antibacterial effect, such as transition metals, such as manganese oxide or oxides of molybdenum or tungsten may be added as fillers. Usual tablet excipients or also activated carbon as well as mixtures thereof may be used as organic fillers. Usual table excipients know in the pharmaceutical field may comprise binding agents, decomposing agents or disintegrants, respectively, gliding agents, lubricants, retarding excipients, such as cellulose, microcrystalline cellulose, hydroxypropyl cellulose, methyl cellulose, hydroxypropyl methyl cellulose, ethyl cellulose, natrium carboxymethyl cellulose, lactose, polyvinylpyrrolidone (PVP), povidone, gelatine, cellulose ether, holocellulose, polyacrylic acid (Carbopol® 934), natrium carboxymethyl starch, gum arabic, dextrin, starch, such as maize, potato or wheat starch, magnesium stearate, calcium behenate, glycerol monostearate, stearin, natrium dodecyl sulphate, magnesium dodecyl sulphate, talcum and mixtures comprising at least two of the fillers.

A subject matter of the invention is retraction paste comprising

- i) 10 to 25% by weight of at least one astringent compound, in particular 10 to 20% by weight,
- ii) 50 to 75% by weight fillers comprising mica and kaolinite, in particular 50 to 65% by weight, and optionally further inorganic and/or organic fillers that may be present as part of the fillers at 0 to 10% by weight, based on the total composition,
- iii) 10 to 35% by weight protic liquid, in particular 15 to 28% by weight, preferably 16 to 28 by weight, and
- iv) 0 to 10% by weight pigments, dye and/or rheology additive,
- ii) the fillers comprising kaolinite and mica in the ratio of 4:1 to 1.5:1, in particular 3.5:1 to 2:1, preferably 3:1 to 1.5:1, and, the total composition of components i) to iv) in the retraction paste amounting to 100% by weight.

Astringent compounds that may be considered include those listed below. For example, aluminium sulphate can be used as a mild astringent, that also acts as an antiseptic. Aluminium sulphate causes haemostasis through a weak vasoconstrictor effect as well as precipitation of tissue proteins, tissue contraction, inhibits the transcapillary flow of plasma proteins and thereby stops capillary bleeding.

In general, the astringent compound may be selected from organic astringent compounds, inorganic astringent compounds and mixtures of at least two of the compounds. In this context, it is preferred for the organic astringent compounds to be present with a content of 1 to 25 by weight, preferably of 3 to 20% by weight in the total mixture of 100% by weight. A particularly preferred organic compound is e.g. tanning agent, such as tannin and/or tannic acid. An inorganic astringent compound or a mixture is preferably present from 5 to 25% by weight, preferably from 10 to 25% by weight in the total mixture of 100% by weight.

According to the invention, i) the at least one astringent compound or a mixture of astringent compounds may comprise

- at least one inorganic astringent salt comprising aluminium salt, in particular comprising aluminium sulphate, ammonium aluminium sulphate ($NH_4Al[SO_4]_2$), potassium aluminium sulphate ($KAl[SO_4]_2$), such as in particular $KAl(SO_4)_2$ 0.12 $H_2O$, aluminium acetate, aluminium trichloride, aluminium trichloride hexahydrate, iron (III) salt, in particular comprising iron (III) chloride ($FeCl_3$), preferably iron (III) salt hydrate, natrium chloride, manganese salt or zinc salt, such as zinc chloride ($ZnCl_2$), zinc oxide, heavy metal salt, as well as solvate and/or hydrate of the inorganic astringent salt, and mixtures of at least two of the aforementioned compounds, and/or
- at least one organic astringent compound comprising polyphenols, polyhydroxyphenols, tanning agents, such as tannins, tannic acid ($C_{76}H_{32}O_{46}$), octenidine salt, octenidine HCl, in particular octenidine 2 HCl, tranexamic acid (trans-4-(aminomethyl) cyclohexane carboxylic acid), c-aminocaproic acid, chitosan, polysaccharides having a dehydrating effect, as well as solvate and/or hydrate of the organic astringent compound, and/or mixtures of at least two of the aforementioned astringent compounds. Likewise, mixture of inorganic and organic astringent compounds may be used. Likewise, adrenaline and optionally with alum (potassium aluminium salt ($KAl(SO_4)_2$)) may be used as astringent compound in the retraction paste.

An aluminium trichloride, in particular aluminium trichloride hexahydrate is preferably used according to the invention.

Tanning agents may also be used as astringent compounds. Tanning agents cause precipitation of tissue proteins when contacting them. Tanning agents comprising hydrolysable tanning agents, such as pyrogallol-type tannins, hardly hydrolysable tanning agents, such as algal tanning agents, and also non-hydrolysable tanning agents, such a catechin tanning agents. Tannins, found in the stems and berry skins of grapes, also have astringent, anti-inflammatory, antibacterial and antiviral effects.

Chitosan and chitosan hydrogel can also be used as haemostatics. Chitosan is a poliglusam por poly-D-glucosamine or polyglucosamine, a naturally occurring biopolymer that consists of β-1,4-glycosidically linked N-acetyl glucosamine residues. Chitosan may be used due to its adsorbing, haemostatic, antimicrobial and remedial effect. Plant-based polysaccharides may also be used as astringent compound due to its dehydrating effect. Such a polysaccharide may be derived from plant starch. Such a polysaccharide, in particular a hydrophilic polysaccharide with very high water absorption capacity, initiates a dehydration process on contact with blood. In this way, the liquid components of the blood are extracted and enclosed in a gel matrix within seconds. This leads to a concentration of fibrin, thrombin and red blood cells, and to endogenous clot formation and haemostasis. The polysaccharide can be obtained from plant starch. The saccharide may preferably be present in the retraction paste in the from of particles with 20 nm to 10 millimetres.

In addition, buffers may be used for adjusting the pH value of the retraction paste. Phosphate buffer, phosphate citrate buffer, 4-(2-hydroxyethyl)-1-piperazine ethane sulfonic acid, 4-(2-hydroxyethyl)-piperazine 1-propane sulfonic acid, 2-(N-morpholino)-ethane sulfonic acid, carbonic acid silicate buffer and/or carbonic acid bicarbonate systems may be used as buffers.

Compounds or compositions of these compounds that are able to form so-called oleogels are in particular considered as rheology additive. Presently, a gel is defined as a gelled liquid that may by means of suitable swelling agents. A hydrophilic gel is referred to a s hydrogel and a lipophilic gel is referred to as oleogel. Hydrophilic gels in the gel composition usually comprise water, glycerol or propylene glycol which may be gelled along with swelling agents, such as poloxamers, starch, cellulose derivatives, carbomers or magnesium aluminium silicates. Lipophilic gels usually comprise paraffin oil optionally with polyethylene or fatty oils with colloidal silicon dioxide, aluminium or zinc soaps.

According to a particularly preferred embodiment, the retraction paste comprises as rheology additive paraffin and optionally polyethylene. The retraction paste preferably comprises a paraffin of a viscosity of 25 to 3020 mPas. In general, the retraction paste may comprise liquid paraffins (Paraffinum perliquidum), oily or pasty paraffins (Paraffinum subliquidum) or solid paraffins (Paraffinum solidum) and/or mixtures of at least two of the said paraffins. The paraffin may correspond to CAS-8012-95-1. A preferred combination of rheology additives comprises Paraffinum liquidum and polyethylene.

Moreover, the rheology additive may comprise petroleum jelly, preferably with a melting range from 38 to 58° C. The petroleum jelly may additionally consist at 70 to 90% by weight of a liquid part of strongly branched iso-paraffins and olefins and as solid part 10 to 30% by weight of long-chain components, such as n-paraffins and lightly branched iso-paraffins. The CAS number for petroleum jelly is 8009-03-8.

The retraction paste may comprise as further rheology additive silicone oil, such as polydimethyl siloxane, terminally olefinically functionalised polydimethyl siloxanes, preferably vinyl-terminated polydimethyl siloxanes.

Preferably, the retraction paste comprises iv) 0.1 to 5% by weight pigments, dye and/or rheology additive, the rheology additives comprising paraffin, petroleum jelly and/or silicone oil or mixtures of at least two of the aforementioned rheology additives. In this context, it is further preferred for the rheology additives to be present at 0.01 to 2.5% by weight in the total composition of 100% by weight, and for component iv) to be present at 0.1 to 10% by weight comprising the rheology additives.

Kaolinite belongs to the section of lamellae silicates (phyllosilicates) in the class of silicates and germanates. Kaolinite is assigned to the phyllosilicates with kaolinite layers due to its structure. Kaolinite has tetrahedral or octahedral layers that are present in a ratio of 1:1. The crystal structure of kaolinite consists of a tetrahedral layer linked to an octahedral layer. The tetrahedral layer consists of tetrahedrons linked by basal oxygens and occupied exclusively by silicon. The octahedral layer consists of edge-linked octahedrons occupied exclusively by aluminium. Kaolinite can have the molecular formula $Al_4[(OH)_8|Si_4O_{10}]$. Kaolinite is a typical two-layer clay mineral.

In mica, each octahedral layer is enclosed by two silicate layers. The silicate tetrahedrons are connected to the octahedral layer with their free tip in which an oxygen is located. Mica has a ratio of silicate to octahedral layers of 2:1. Mica structural units, also as TOT or 2:1 layers are stacked on top of each other in the direction of the crystallographic c-axis and may be twisted around the c-axis and form mica polytypes. The mica may comprise A-polytypes, B-polytypes and also mixed polytypes.

Micas are thin tough and elastic lamellae fissile along their planes. Micas may have the general chemical formula $XY_2(OH, F)_2Z' Z''_3 O_{10}$ with $X=K^+$, $Na^+$, $Rb^+$, $Cs^+$, in specific cases $Ba^{2+}$ with a coordination number 12, $Y=Al^{3+}$, $Fe^{3+}$, $Cr^{3+}$, $Mn^{3+}$, $V^{3+}$, $Ti^{3+}$, $Mn^{2+}Li^+$, optionally $Zn^{2+}$ with a coordination number 6, $Z'=Al^{3+}$, often $Si^{4+}$, or also $Fe^{3+}$, $Mn^{3+}$, $Ti^{3+}$ with a coordination number 4 and $Z''=Sr^{1+}$.

Known micas comprise muscovite and potash mica. $[KAl_2AlSi_3O_{10}(OH)_2]$ may be the molecular formula of muscovite. Further micas comprise phlogopite or magnesium mica, paragonite, biotite, polylithionite, margarite (calcium mica), sericite and vermiculite.

Particularly preferably, the fillers are selected from kaolinite and mica, preferably in the ratio of 4:1 to 3:2. The particular ratio of kaolinite to mica preferably in combination with the rheology additive(s) according to the invention enables adjustment of a consistency of the retraction paste in which the layers of the fillers used can interlock against each other and thus form an easy applicable and yet stable paste.

A retraction paste according to the invention has a mixing discus according to DIN ISO 4823 2015-08 with an apparatus according to A.1 (two quadratic glass plates approx. 60×60 mm, minimum distance 3 mm, amount of sample 0.5+1-0.02 ml, period of loading 5 min, measurement temperature: 23° C.+1-2° C.) and a load of 2500+1-5 g modified to DIN ISO 4823 2015-08, in particular to develop the force applied to the retraction paste. Diameters of a mixing discus according to the aforementioned testing methods of 10 to 25 mm, in particular of 14 to 24 mm, preferably of 15 to 21 mm, may be obtained with the retraction pastes according to the invention. A mixing discus with this diameter is preferably well-suited for an application from a syringe or PLT. In a further differentiation, it is advantageous for an application from a syringe to choose a retraction paste forming a discus having a diameter of 18 to 24 mm, in particular 19 to 21 mm. A retraction paste having a mixing discus of 14 to 19 mm according to the above method, in particular 15 to 18 mm, is most suitable for the PLT. The consistency of the retraction paste in these cases is suitable to form an at least 2 cm long stable thread-like structure from containers, such as syringes, ampoules, cartridges, in particular PLT-cartridges via a canula having an inner diameter of 0.4 mm+/−0.025 mm. An advantage of this thread-like structure of the retraction paste is that it can be brought into the sulcus where it expands by absorbing the fluid in the sulcus and dilates the sulcus, as well as induces haemostasis at the same time.

A particularly preferable retraction paste comprises i) 10 to 20% by weight of at least one astringent compound ii) as fillers 30 to 56% by weight kaolinite and 10 to 28% by weight mica, iii) 10 to 30% by weight protic liquid, in particular 18 to 28% by weight, and iv) 0 to 10% by weight pigments, dye and/or rheology additive, ii) the fillers comprising kaolinite and mica in the ratio of 4:1 to 3:2.

A particularly preferable retraction paste comprises i) 12 to 20% by weight of at least one astringent compound, ii) 55 to 65% by weight fillers, comprising kaolinite and mica in the ratio of 4:1 to 1.5 to 1, iii) 20 to 30% by weight protic liquid, in particular 18 to 28% by weight, and iv) 0.1 to 5% by weight pigments, dye and/or rheology additive.

Moreover, the retraction paste preferably comprises v) 0 to 25% by weight gel forming agent, the total composition of components i) to v) in the retraction paste amounting to 100% by weight.

A preferred protic liquid iii) comprises water, C1 to C4 alcohols, in particular mono-functional alcohols, C1 to C4 polyols, glycerol and mixtures of at least two of the aforementioned compounds. Particularly preferred is water, in particular distilled water.

Preferably, antimicrobial, antibacterial, antiviral pigments and dyes are chosen as pigments and dyes. Violacein may be an example of the phtalocyanine used.

Likewise subject matter of the invention is a method for producing the retraction paste as well as a retraction paste obtainable according to the method, in which i) 10 to 20% by weight of at least one astringent compound or a mixture of astringent compounds, ii) 50 to 75% by weight fillers, the fillers comprising kaolinite and mica in the ratio of 4:1 to 1.5:1, iii) 10 to 35% by weight protic liquid, in particular 18 to 28% by weight, and iv) 0 to 10% by weight pigments, dye and/or rheology additive, are being mixed, in particular at first components i), ii) are being mixed, and subsequently component iii) and optionally iv) are being mixed thereto, alternatively preferably components i) to iv) may be mixed, and the total composition of components i) to iv) in the retraction paste amounting to 100% by weight.

Furthermore, a subject matter of the invention is a kit comprising a container, the container comprising a syringe, syringe cylinder, cartridge or ampoule, and the container further comprising a retraction paste according to the invention. The container may comprise a cartridge with canula, a syringe having a screw connection, a syringe having a Luer lock connection, a syringe having a bayonet connection or an ampoule having a plunger and an ampoule closure. Preferably, the kit comprises a syringe or an ampoule with retraction paste, as well as a canula having a screw connection, canula having a Luer lock connection, or a canula having a bayonet connection for connecting with the crew connection or the bayonet connection of the syringe or a canula for fastening at the ampoule closure.

Likewise a subject matter of the invention is a retraction paste, in particular as medical composition, being used for medical treatment, in particular dental treatment, in particular the retraction paste is used for the treatment of bleedings of the gingiva as an agent for haemostasis.

The invention is explained in more detail by the following examples without restricting the invention to these examples.

EXEMPLARY EMBODIMENTS

The below retraction pastes were produced and their consistency and thus their behaviour under pressure was determined according to the modified method of DIN ISO 4823 2015-08 with the modified load with a weight of 2500+/−5 g. In addition, the stability of the pastes was determined with the method described below.

TABLE 1

Retraction Pastes

| Retraction paste | Paste 1 wt.-% | Paste 2 wt.-% |
|---|---|---|
| kaolin | 37.00-40.00 | 40 |
| mica | 17.00-20.00 | 18 |
| pigment/dye (blue, phthalocyanine) | 0.6-1.00 | 0.8 |
| rheology additive | 0.05-1.5 | 1 |
| water | 16.00-28.00 | 26.2 |
| aluminium chloride hexahydrate ($AlCl_3$•6 $H_2O$) | 12.00-18.00 | 14 |
| sum | 100 | 100 |

TABLE 2

Retraction Pastes

| Retraction paste | Paste 3 wt.-% | Paste 4 wt.-% |
|---|---|---|
| kaolin | 38 | 40 |
| mica | 19 | 18 |
| pigment/dye (blue, phthalocyanine) | 0.75 | 0.8 |
| rheology additive | 1 | 0 |
| water | 26.5 | 26.20 |
| aluminium chloride hexahydrate ($AlCl_3$•6 $H_2O$) | 14.75 | 14 |
| sum | 100 | 100 |

TABLE 3

Retraction Pastes

| Retraction paste | Paste 5 wt.-% |
|---|---|
| kaolin | 42 |
| mica | 21 |

TABLE 3-continued

| Retraction Pastes | |
|---|---|
| Retraction paste | Paste 5 wt.-% |
| pigment/dye (blue, phthalocyanine) | 0.75 |
| rheology additive | 1 |
| water | 20.5 |
| aluminium chloride hexahydrate ($AlCl_3$•6 $H_2O$) | 14.75 |
| sum | 100.00 |

TABLE 4

| Comparative Example (VG) Retraction Pastes | | |
|---|---|---|
| Retraction paste | VG1 wt.-% | VG1 wt.-% |
| kaolin | 28.50 | 19 |
| mica | 28.50 | 38 |
| pigment/dye | 0.75 | 0.75 |
| rheology additive | 1 | 1 |
| water | 26.5 | 26.5 |
| aluminium chloride hexahydrate ($AlCl_3$•6 $H_2O$) | 14.75 | 14.75 |
| sum | 100 | 100 |

To determine the consistency and thus their behaviour under pressure of the retraction pastes, the diameter of a mixing discus was determined each as well as the force required to press the retraction paste through a defined gap to simulate the conditions in the sulcus after application from a cannula.

A mixing discus each was produced from the retraction pastes according to DIN ISO 4823 2015-08 with an apparatus according to A.1. Measurement conditions: between two quadratic glass plates approx. 60×60 mm, minimum distance 3 mm, amount of sample 0.5+/−0.02 ml, period of loading 5 min, measurement temperature: 23° C. +/−2° C.,) load with a weight modified to DIN ISO 4823 2015-08 of 2500+/−5 g to develop the force applied to the retraction paste.

A mixing discus having a diameter of 19 to 21 mm is obtained with the retraction pastes Paste 2 to 4 each. The consistency of these retraction pastes is exceptionally well-suited to form an at least 2 cm long stable thread-like structure from a syringe having a blunt bent canula that has an inner diameter of 0.4 mm. In doing so, the retraction paste as thread-like structure can be brought into the sulcus and can dilatate the sulcus, as well as induce haemostasis.

A retraction paste by which a mixing discus having a diameter of up to 24 mm is being obtained is considered particularly advantageous for applications to widen the sulcus.

An appropriate testing method for simulation the conditions was developed to be able to determine the stability of the retraction paste in the sulcus after application. For this purpose, the effort maximally required to axially bring in a cylindrical plunger having a 5 mm diameter into the surface of a cylindrical cavity filled with retraction paste, having a diameter of 8 mm and a depth of 4 mm, by 2 mm (indicated as max. force in Newton at 2 mm penetration depth (max. force (N)/2 mm)). In the aforementioned measurement setup, the retraction paste is pressed through a radially circumferenting 1.5 mm wide gap out of the cavity (measurement device: TA.XT.plus Texture Analyser of the company Stable Micro Systems, testing speed: 0.10 mm/sec, way: 2.000 mm, tool: 5 mm plunger stainless steel, measurement cylinder: 5 mm diameter, a disc having a cavity serves as sample holder: diameter 8 mm and height 4 mm, retraction paste is filled into the cavity, the surface is smoothed with a planar object and overlapping material is removed). The measurement plunger is axially pressed into the retraction paste with 0.10 mm/sec 2.000 mm and the force to be maximally applied is being determined.

Pastes 2 and 4 are particularly well-suited for application from a syringe. Paste 5 is very well adjusted for an application from a PLT.

In Table 5, simulation of stability shows significantly higher values in the range of 3,0 to 10.9 for the pastes according to the invention than for the comparative examples having a different ratio of kaolin to mica, the values of which amount to 1.6 and 2.3. Consequently, retraction pastes having a very good stability can be obtained with the ratio according to the invention of kaolin to mica, in particular in interaction with a defined water content.

TABLE 5

| | Retraction pastes | | | | | |
|---|---|---|---|---|---|---|
| | VG1 | VG2 | Paste 2 | Paste 3 | Paste 4 | Paste 5 |
| mixing discus (mm) | 21.0 | 21.5 | 20 | 20.5 | 19.5 | 15 |
| mean value max. force (N)/2 mm | 2.3 | 1.6 | 3.8 | 3.0 | 4.2 | 10.9 |

EMBODIMENTS OF THE INVENTION

Figure 1A:
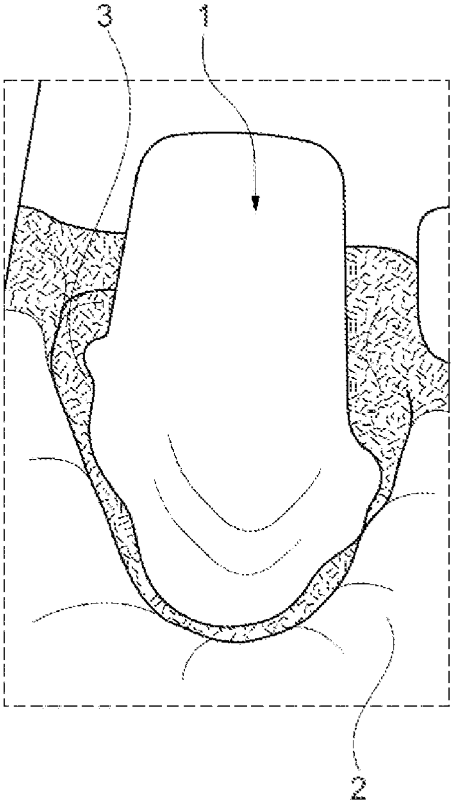
FIGS. 1*a* and 1*b* show a clinical example fora gingival retraction of the sulcus 3 by means of a retraction paste.
Figure 1B:
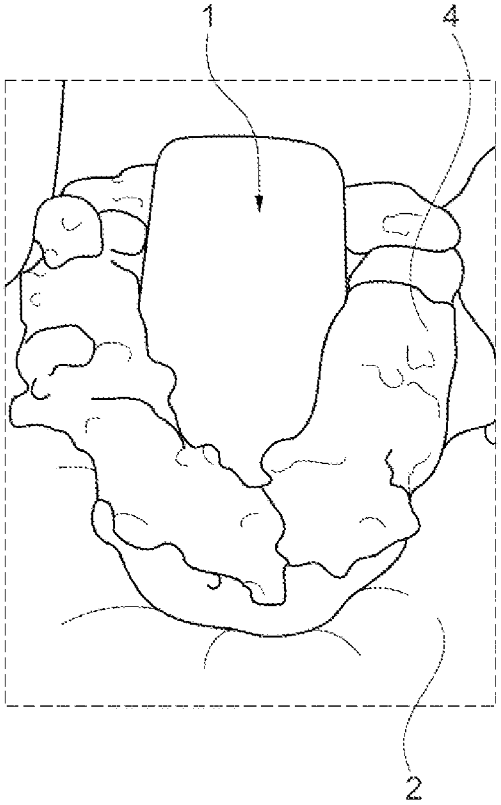

FIG. 1*a* represents a clinical example in which an exposed ground tooth stump 1 with preparation margin and bleeding sulcus 3 and surrounding gingiva 2 form the starting situation for application of a retraction measure. The sulcus 3 of the gingiva is then filled with retraction paste 4 according to the invention for preparation of the sulcus for taking an impression of the preparation margin of the ground tooth stump. FIG. 1*b* shows the retraction paste 4 in the sulcus of the gingiva 2. The retraction paste 4 has been syringed in the sulcus around the tooth stump and its preparation margin. The whole preparation process in the bleeding sulcus is explained in more detail in FIGS. 5*a* to 5*d*.

Figure 2A:
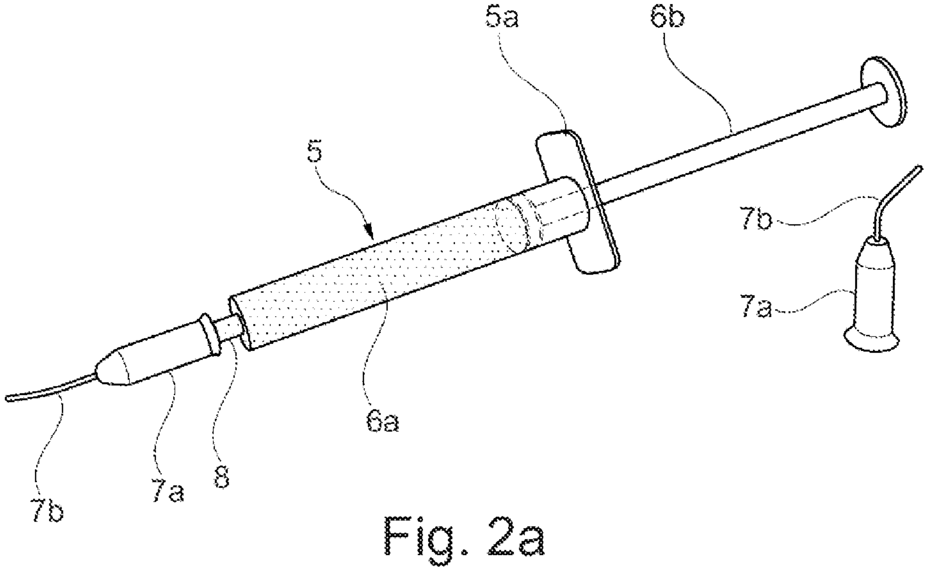
FIGS. 2*a* and 2*b* show a kit each comprising a syringe 5 having a screw connection and a syringe 9 having a bayonet connection.
Figure 2B:
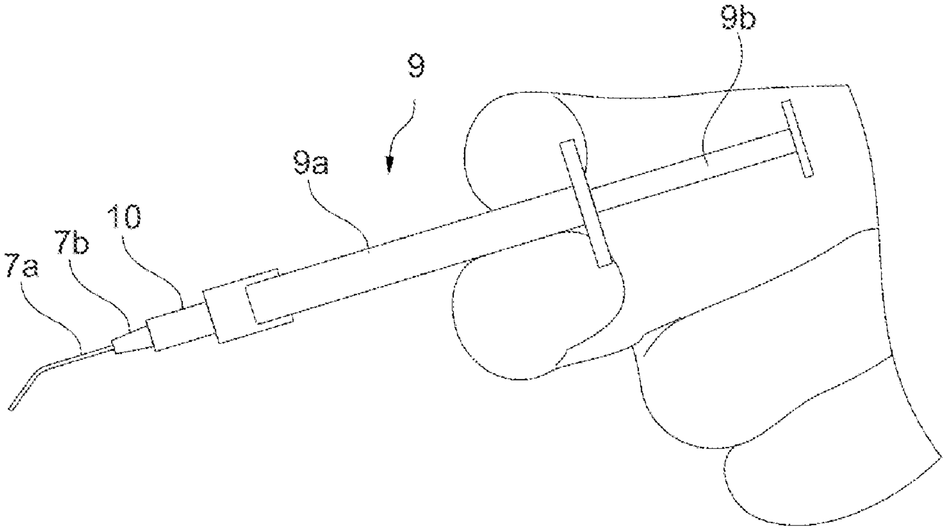

FIG. 2*a* represents a kit comprising a syringe 5 having a screw connection the syringe cylinder 6*a* of which is filled with the retraction paste according to the invention. A canula 7*a* having an inside thread as screw connection and a blunt canula 7*b* is distally fastened to the screw connection 8 of the syringe 5. FIG. 2*b* represents a syringe 9 having a bayonet connection. The syringe body 9*a* distally has a bayonet connection 10, a canula 7*b* having a bayonet connection and a blunt canula 7*a* is fastened to which. The two syringes 5 and 9 have a proximally situated handle 5*a* or 9*a*, respectively, wherein the retraction paste can be applied through the blunt canula 7*a* into a sulcus by pressing and sliding in the syringe piston 6*b* or 9*b*, respectively. The retraction paste is obtainable in cartridges, ampoules or syringes and is applied into the gingival sulcus via a canula. The retraction paste is left there for about 2 minutes, subsequently rinsed out with water, see FIG. 5*d*. Subsequently, the sulcus may be carefully dried using an air blower.

Figure 3A:
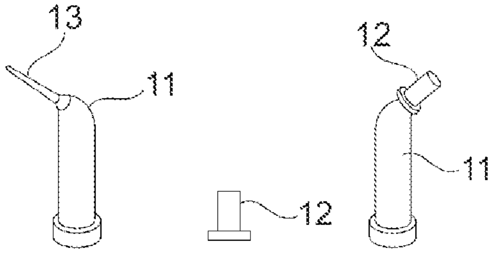
FIGS. 3*a* and 3*b* show cartridges 11 having a canula 13 as well as a composite gun 14 with inserted cartridge 11 having a canula 13.
Figure 3B:
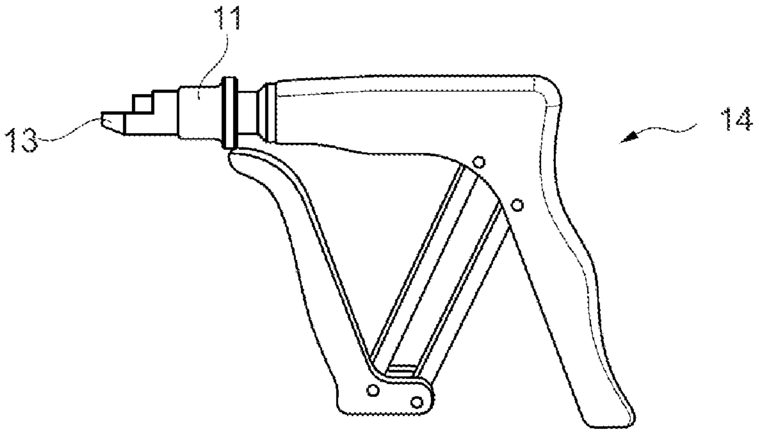

FIG. 3*a* represents cartridges 11 having a canula 13 and a put-on closure 12. The cartridges are filled with retraction paste. FIG. 3*b* shows a composite gun 14 or PLT dispenser, respectively with inserted cartridge 11 having a canula 13.

Figure 4A:
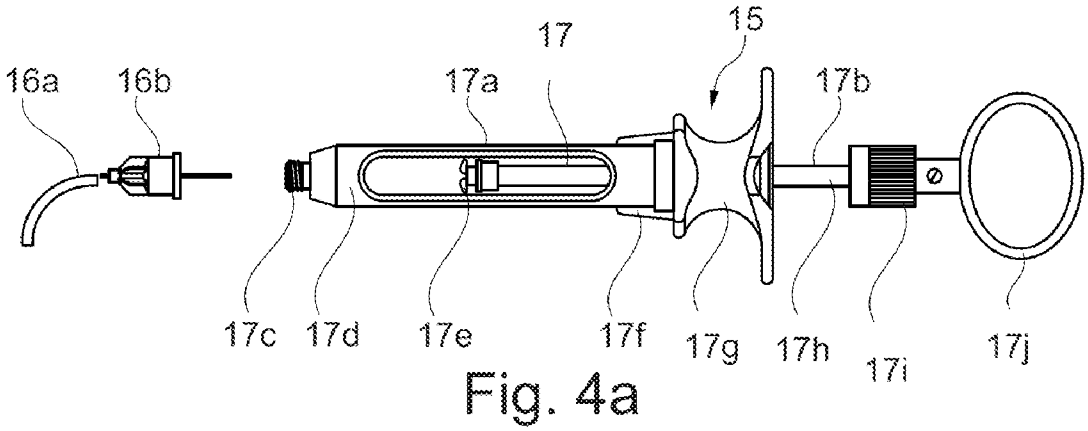
FIGS. 4*a* and 4*b* show a cylinder piston syringe 15 having a cylinder ampoule 17 as well as an ampoule 18 having a displaceable plunger.
Figure 4B:
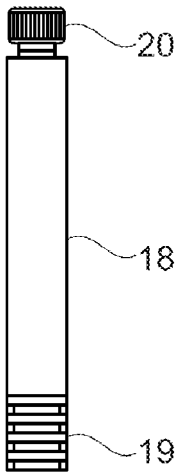

FIGS. 4*a* and 4*b* show a cylinder piston syringe 15 having a cylinder ampoule 17 as well as an ampoule 18 having a displaceable plunger and an ampule closure 20.

FIG. 4*a* shows a cylinder piston syringe 15 having a cylinder ampoule 17, canula 16*a* having a connection and a bent blunt application canula 16*b* for the cylinder piston syringe 15. A cylinder ampoule 17 is inserted into the cylinder piston syringe 15. The cylinder piston syringe 17 has an inlet seat 17*a* for a cylinder ampoule 17, piston rod with handle 17*b*, screw thread for canula 17*c*, cylinder ampoule holder 17*d*, distal end, in particular with aspiration hooks 17*e* of the piston rod of the cylinder piston syringe, joint having a folding mechanism for opening the cylinder ampoule holder 17*f*, handle e.g. finger support 17*g*, piston rod 17*h*, knurled-head screw 17*i* for fastening the ampoule 17 at the distal end of the piston rod of the cylinder piston syringe, and a handle e.g. thumb plate ring 17*j*. A cylinder piston syringe enables a very controlled pressure application and thus a high-precision discharge of the retraction paste by means of displacing the displaceable plunger 19 in the cylinder ampoule 17 or ampoule 18, respectively, via the canula into the sulcus. An ampoule 18 has a closure 19 that is removed before insertion into the cylinder piston syringe 15.

FIGS. 5*a*, 5*b*, 5*c* and 5*d* show a kit according to the invention of a syringe 5 having a screw connection that has a syringe cylinder filled with a retraction paste according to the invention, a retraction gel is also synonymous to a retraction paste. The syringe cylinder 6*a* of the syringe 5 is filled with retraction paste. The syringe has a handle 5*a* as well as a screwed-on canula 7*a* having a blunt bent canula 7*b*. The retraction paste 4—FIGS. 5*b* and 5*c*—is syringed into the bleeding sulcus 3—FIG. 5*a*—or the sulcus is filled with haemostatic retraction paste 4, respectively, via the blunt and bent application canula 7*b*. Then, the astringent effect of the retraction paste leads to haemostasis in the widened sulcus. The paste causes the sulcus to remain widened by means of its defined adjusted viscosity and stability. The added astringent agents, such a aluminum chloride, causes haemostasis.

Figure 5A:
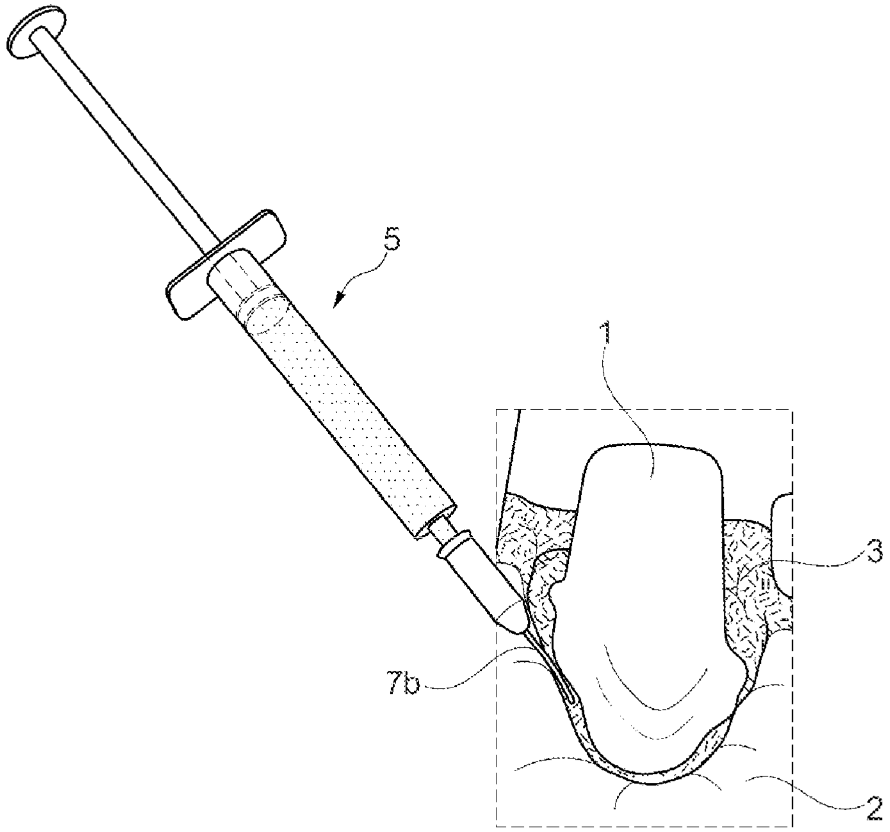
FIGS. 5*a* to 5*d* show use of the retraction paste 4 according to the invention.
Figure 5B:
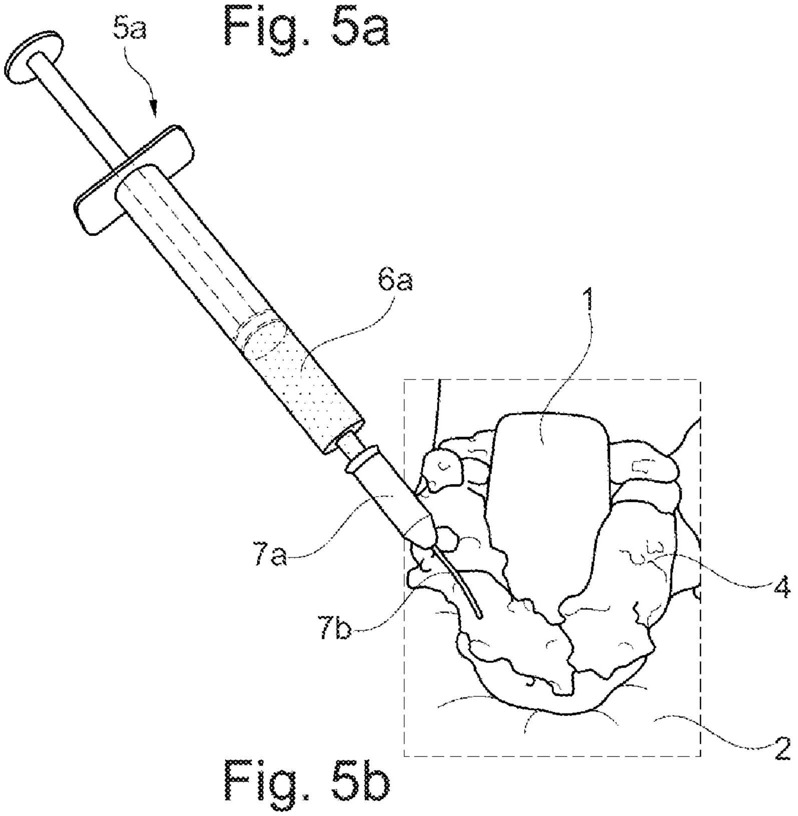
Figure 5C:
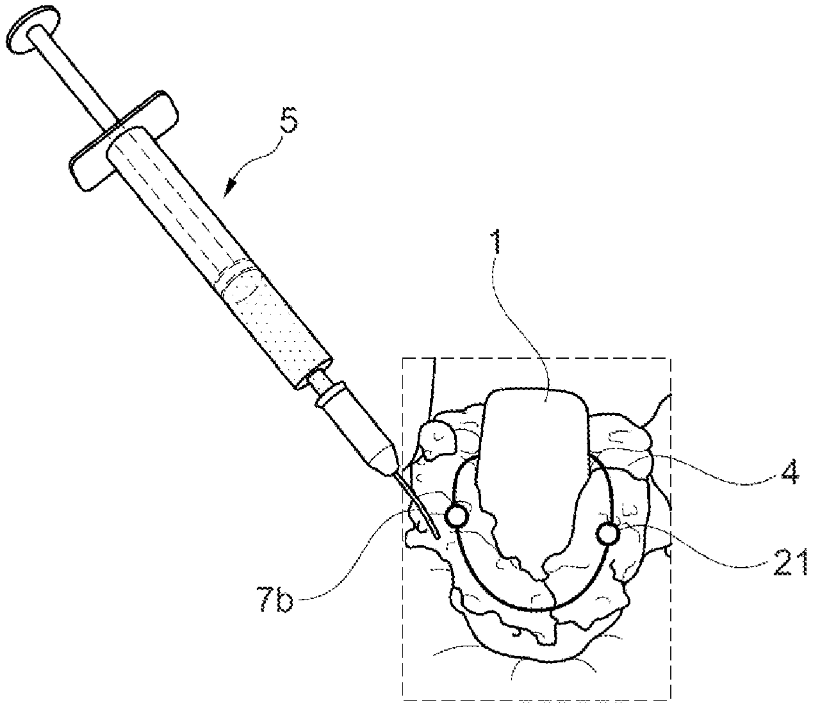

FIG. 5*c* represents a combination of thread techniques and retraction pastes. In case of a deeper and wide gingival sulcus, usually a thread having a smaller diameter is initially inserted into the sulcus to displace the gingiva vertically. The thread shall comprise the whole circumference of the tooth stump without overlapping of the thread ends. The retraction paste 4 is inserted into the sulcus via the thread 21 being laid around the tooth stump 1 and subsequently dilates the sulcus, so that the preparation margin is exposed for later impression.

Figure 5D:
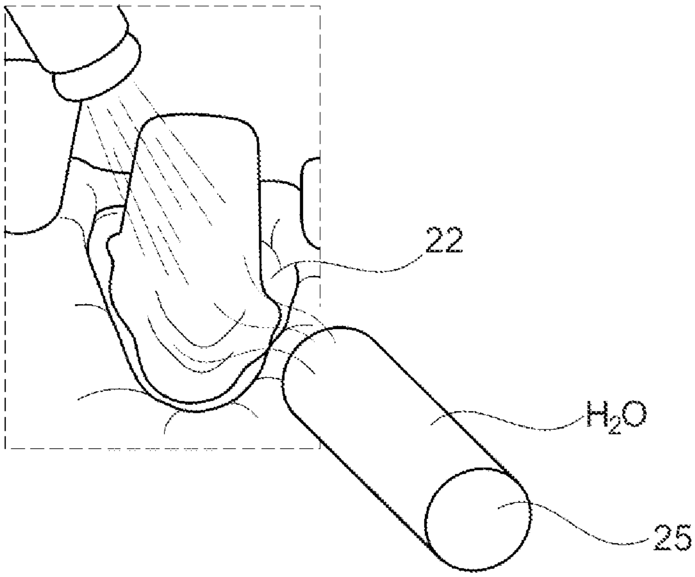

In FIG. 5*d*, the retraction paste is removed from the sulcus after sufficient application time using water or an air-water-stream. The water and the washed away retraction paste is removed with a water-suction appliance 25. After that, the sulcus is dry blowed using a smooth compressed air stream. The sulcus is then dilated 22, i.e. the astringent sulcus is widened and ready for an impression.

FIG. 5*d* after removal of the retraction paste 4, the sulcus 3 is dilatated, dry and free of blood. The preparation margin is well accessible and can be impressed with high accuracy. Any customary impression material can be used for impression. Flexitime® can be used for subsequent impression of the tooth stump as impression material to impress the subgingival preparation margin. In this case, a corrective impression, if appropriate, can be more suitable due to the higher dynamic pressure than a one-sided impression procedure, as especially in precision impression of a subgingival preparation margin it can be the case that the dynamic pressure is too low in one-sided impression to press a sufficient amount of the low viscosity impression material into the sulcus difficult to access.

The retraction paste according to the invention has a very good consistency and convinces in a very easy time-saving handling as well as a low after-bleeding, in particular a prolonged haemostasis as well as an effective sulcus opening.

LIST OF REFERENCE NUMERALS

1 ground tooth stump with preparation margin
2 gingiva
3 sulcus (bleeding sulcus)
4 retraction paste
5 syringe having a screw connection
5*a* handle of the syringe
6*a* syringe cylinder
6*b* syringe piston/syringe plunger with handle
7*a* canula, screwable canula 7*a* or canula having a bayonet connection
7*b* blunt bent application canula
8 screw connection at syringe cylinder
9 syringe having a bayonet connection
9*a* syringe cylinder having a bayonet connection
9*b* Syringe piston/syringe plunger with handle
10 bayonet connection
11 cartridge with canula 13 and closure 12 for the canula 13 inlet nozzle
12 closure for canula at cartridge
13 canula at cartridge
14 composite gun
15 cylinder piston syringe
16*a* canula having a connection for cylinder piston syringe 15
16*b* application canula
17 cylinder ampoule
17*a* inlet seat for cylinder ampoule
17*b* piston rod with handle
17*c* screw thread for canula
17*d* cylinder ampoule holder
17*e* distal end of the (aspiration hooks) piston rod of the cylinder piston syringe
17*f* joint having a folding mechanism for opening the cylinder ampoule holder
17*g* handle e.g. finger support 17*h* piston rod 17*i* knurled-head screw for fastening the ampoule at the distal end of the piston rod, of the cylinder piston syringe 17*j* handle e.g. thumb plate ring, controlled pressure application

18 ampoules having a displaceable plunger 19 and having an ampoule closure 20

19 ampoule plunger

20 ampoule closure

21 thread under retraction paste

22 astringend dilated sulcus ready for impression

25 water-suction applicance

The invention claimed is:

1. Retraction paste, comprising:

i) 1 to 25% by weight of at least one astringent compound, ii) 50 to 75% by weight fillers, iii) 10 to 35% by weight protic liquid, and iv) 0 to 10% by weight pigments and/or dye and comprising rheology additive, wherein, when the rheology additive is present, the rheology additive is present from 0.01 to 2.5% by weight in a total composition of 100% by weight, wherein the fillers comprise kaolinite and mica at a ratio of 4:1 to 1.5:1 and, the total composition of components i) to iv) in the retraction paste amounts to 100% by weight.

2. Retraction paste according to claim 1, which comprises:

i) 10 to 25% by weight of at least one astringent compound, ii) 50 to 70% by weight fillers, iii) 15 to 30% by weight protic liquid, and iv) 0 to 10% by weight pigments and/or dye and rheology additive, wherein, when the rheology additive is present, the rheology additive is present from 0.01 to 2.5% by weight in the total composition of 100% by weight, wherein the fillers comprise kaolonite and mica at the ration of 4:1 to 1.5:1 and, the total composition of components i) to iv) in the retraction paste amounts to 100% by weight.

3. Retraction paste according to claim 1, wherein the kaolinite has an average particle size $D_{50}$ of 0.01 to 100 micrometers and optionally with $D_{70}$ less than 45 micrometers.

4. Retraction paste according to claim 1, wherein the mica has an average particle size of 0.01 to 100 micrometers and optionally with $D_{70}$ less than 4 micrometers.

5. Retraction paste according to claim 1, wherein the at least one astringent compound or a mixture of at least two astringent compounds comprises inorganic astringent salt comprising aluminium salt, iron (III) salt natrium chloride, manganese salt or zinc salt, heavy metal salt, as well as solvate and/or hydrate of the inorganic astringent salt, and/or organic astringent compound comprising polyphenols, polyhydroxyphenols, tanning agents, tannic acid, octenidine salt, octenidine 2 HCl, tranexamic acid (trans-4-(aminomethyl) cyclohexane carboxylic acid), ε-aminocaproic acid, chitosan, polysaccharides having a dehydrating effect, as well as solvate and/or hydrate of the organic astringent compound, and/or mixtures of at least two of the afore-mentioned astringent compounds.

6. Retraction paste according to claim 1, the retraction paste further comprising:

v) 0 to 25% by weight gel forming agent, the total composition of components i) to v) in the retraction paste amounting to 100% by weight.

7. Retraction paste according to claim 1, wherein the protic liquid comprises water, C1 to C4 alcohols, C1 to C4 polyols, and mixtures of at least two of the afore-mentioned compounds.

8. Retraction paste according to claim 1, wherein the protic liquid is water.

9. Method for producing the retraction paste according to claim 1, comprising mixing the components:

i) 10 to 20% by weight of at least one astringent compound, ii) 50 to 75% by weight fillers, the fillers comprising kaolinite and mica in the ratio of 4:1 to 1.5:1, iii) 10 to 30% by weight protic liquid, and iv) 0 to 10% by weight pigments, dye and/or rheology additive, and the total composition of components i) to iv) in the retraction paste amounting to 100% by weight.

10. Kit comprising a container, the container comprising a syringe, syringe cylinder, cartridge or ampoule, the container each comprising a retraction paste according to claim 1.

11. Kit according to claim 10, wherein the kit comprises a cartridge with canula (11), a syringe having a screw connection (5), a syringe having a Luer lock connection, a syringe having a bayonet connection (9) or an ampoule having a plunger and an ampoule closure (18).

12. Kit according to claim 10, comprising a canula having a screw connection, canula having a Luer lock connection, or a canula having a bayonet connection for connecting with the screw connection, Luer lock connection or the bayonet connection of the syringe or a canula for fastening at the ampoule closure.

13. A method for treating a medical condition in a patient in need thereof, said method comprising applying a retraction paste according to claim 1 to the patient.

14. Method according to claim 13, which is carried out for the treatment of bleedings of the gingiva in the patient and the retraction paste is applied to the patient as an agent for haemostasis.

* * * * *